US011186613B2

(12) United States Patent
Ito et al.

(10) Patent No.: US 11,186,613 B2
(45) Date of Patent: Nov. 30, 2021

(54) SOLID-PHASE SUPPORT COMPRISING IGG-BINDING PEPTIDE, AND METHOD FOR SEPARATING IGG

(71) Applicants: Kagoshima University, Kagoshima (JP); Daicel Corporation, Osaka (JP)

(72) Inventors: Yuji Ito, Kagoshima (JP); Seiichi Uchimura, Hyogo (JP)

(73) Assignees: Kagoshima University, Kagoshima (JP); Daicel Corporation, Osaka (JP)

( * ) Notice: Subject to any disclaimer, the term of this patent is extended or adjusted under 35 U.S.C. 154(b) by 82 days.

(21) Appl. No.: 16/461,871

(22) PCT Filed: Nov. 17, 2017

(86) PCT No.: PCT/JP2017/041404

§ 371 (c)(1),
(2) Date: May 17, 2019

(87) PCT Pub. No.: WO2018/092867

PCT Pub. Date: May 24, 2018

(65) Prior Publication Data

US 2019/0367560 A1 Dec. 5, 2019

(30) Foreign Application Priority Data

Nov. 18, 2016 (JP) ............................ JP2016-225483

(51) Int. Cl.

| | |
|---|---|
| ***C07K 7/04*** | (2006.01) |
| ***C07K 17/00*** | (2006.01) |
| ***C07K 1/22*** | (2006.01) |
| ***C07K 16/00*** | (2006.01) |
| ***G01N 30/88*** | (2006.01) |
| ***C12N 15/09*** | (2006.01) |
| ***C07K 7/08*** | (2006.01) |
| ***C07K 1/16*** | (2006.01) |
| ***C07K 17/08*** | (2006.01) |
| ***C07K 17/10*** | (2006.01) |

(52) U.S. Cl.

CPC .................. *C07K 7/08* (2013.01); *C07K 1/16* (2013.01); *C07K 17/08* (2013.01); *C07K 17/10* (2013.01)

(58) Field of Classification Search

None

See application file for complete search history.

(56) References Cited

U.S. PATENT DOCUMENTS

| | | | | |
|---|---|---|---|---|
| 2014/0274790 A1 | 9/2014 | Ito | | |
| 2015/0150998 A1* | 6/2015 | Hu | ........................ | A61K 47/62 530/391.5 |

FOREIGN PATENT DOCUMENTS

| | | |
|---|---|---|
| WO | 2011/047215 A1 | 4/2011 |
| WO | 2013/027796 A1 | 2/2013 |

OTHER PUBLICATIONS

Assem et al., "Acetone-Linked Peptides: A Convergent Approach for Peptide Macrocyclization and Labeling," Angew. Chem. Int. Ed. 54: 8665-8668 (Jun. 2015) (Year: 2015).*

Dias et al., "Protein Ligand Design: From Phage Display to Synthetic Protein Epitope Mimetics in Human Antibody Fc-Binding Peptidomimetics," Journal of the American Chemical Society, 128: 2726-2732 (2006).

Kang et al., "Cyclic peptide ligand with high binding capacity for affinity purification of immunoglobulin G," Journal of Chromatography A, 1466: 105-112 (2016).

Wang et al., "A Thiol-Ene Coupling Approach to Native Peptide Stapling and Macrocyclization," Angewandte Chemie International Edition, 54: 10931-10934 (2015).

Office Action issued in related Indian Patent Application No. 201947022859 dated Jul. 27, 2021.

* cited by examiner

*Primary Examiner* — Julie Ha

*Assistant Examiner* — Kristina M Hellman

(74) *Attorney, Agent, or Firm* — Morgan, Lewis & Bockius LLP

(57) ABSTRACT

The present invention provides an IgG-binding peptide which can be used for the purification of IgG and has excellent stability, e.g., alkali stability. The present invention also provides a method for purifying IgG using the IgG-binding peptide. Specifically, the present invention relates to a solid-phase support including an IgG-binding peptide, an IgG separation column including the solid-phase support, a kit including the solid-phase support or the column, and a method for purifying IgG using the solid-phase support or the column.

19 Claims, 4 Drawing Sheets

Specification includes a Sequence Listing.

SEQUENCE LISTING

```
<160> NUMBER OF SEQ ID NOS: 31

<210> SEQ ID NO 1
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 1

Asp Cys Ala Tyr His Xaa Gly Glu Leu Val Trp Cys Thr
1               5                   10


<210> SEQ ID NO 2
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 2

Gly Pro Asp Cys Ala Tyr His Xaa Gly Glu Leu Val Trp Cys Thr Phe
1               5                   10                  15
```

His

<210> SEQ ID NO 3
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine, or derivative thereof

<400> SEQUENCE: 3

Arg Cys Ala Tyr His Xaa Gly Glu Leu Val Trp Cys Ser
1 5 10

<210> SEQ ID NO 4
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine, or derivative thereof

<400> SEQUENCE: 4

Gly Pro Arg Cys Ala Tyr His Xaa Gly Glu Leu Val Trp Cys Ser Phe
1 5 10 15

His

<210> SEQ ID NO 5
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine, or derivative thereof

<400> SEQUENCE: 5

Ser Pro Asp Cys Ala Tyr His Xaa Gly Glu Leu Val Trp Cys Thr Phe
1 5 10 15

His

<210> SEQ ID NO 6
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine, or derivative thereof

<400> SEQUENCE: 6

Gly Asp Asp Cys Ala Tyr His Xaa Gly Glu Leu Val Trp Cys Thr Phe
1 5 10 15

His

<210> SEQ ID NO 7
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 7

Gly Pro Ser Cys Ala Tyr His Xaa Gly Glu Leu Val Trp Cys Thr Phe
1               5                   10                  15

His

<210> SEQ ID NO 8
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 8

Gly Pro Asp Cys Ala Tyr His Xaa Gly Glu Leu Val Trp Cys Ser Phe
1               5                   10                  15

His

<210> SEQ ID NO 9
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 9

Gly Pro Asp Cys Ala Tyr His Xaa Gly Glu Leu Val Trp Cys Thr His
1               5                   10                  15

His

<210> SEQ ID NO 10
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine,
      or derivative thereof

<400> SEQUENCE: 10

Gly Pro Asp Cys Ala Tyr His Xaa Gly Glu Leu Val Trp Cys Thr Phe
1               5                   10                  15

Tyr

<210> SEQ ID NO 11
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine, or derivative thereof

<400> SEQUENCE: 11

Ser Pro Asp Cys Ala Tyr His Xaa Gly Glu Leu Val Trp Cys Thr Phe
1 5 10 15

Tyr

<210> SEQ ID NO 12
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine, or derivative thereof

<400> SEQUENCE: 12

Ser Asp Asp Cys Ala Tyr His Xaa Gly Glu Leu Val Trp Cys Thr Phe
1 5 10 15

Tyr

<210> SEQ ID NO 13
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa is arginine, lysine, leucine, asparagine, or derivative thereof

<400> SEQUENCE: 13

Arg Gly Asn Cys Ala Tyr His Xaa Gly Gln Leu Val Trp Cys Thr Tyr
1 5 10 15

His

<210> SEQ ID NO 14
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa is homoserine
<220> FEATURE:
<221> NAME/KEY: misc_feature
<222> LOCATION: (8)..(8)
<223> OTHER INFORMATION: Xaa is arginine, lysine, leucine, asparagine, or derivative thereof

```
<220> FEATURE:
<221> NAME/KEY: misc_feature
<222> LOCATION: (16)..(16)
<223> OTHER INFORMATION: Xaa is homoserine

<400> SEQUENCE: 14

Gly Xaa Asp Cys Ala Tyr His Xaa Gly Glu Leu Val Trp Cys Thr Xaa
1               5                   10                  15

His


<210> SEQ ID NO 15
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 15

Asp Cys Thr Tyr His Xaa Gly Asn Leu Val Trp Cys Thr
1               5                   10


<210> SEQ ID NO 16
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 16

Asp Cys Ala Tyr His Xaa Gly Asn Leu Val Trp Cys Thr
1               5                   10


<210> SEQ ID NO 17
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof

<400> SEQUENCE: 17

Asp Cys Thr Tyr His Xaa Gly Glu Leu Val Trp Cys Thr
1               5                   10


<210> SEQ ID NO 18
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine,
      or derivative thereof
```

<400> SEQUENCE: 18

Asp Cys Ala Trp His Xaa Gly Glu Leu Val Trp Cys Thr
1 5 10

<210> SEQ ID NO 19
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine, or derivative thereof

<400> SEQUENCE: 19

Asp Cys Thr Tyr Thr Xaa Gly Asn Leu Val Trp Cys Thr
1 5 10

<210> SEQ ID NO 20
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine, or derivative thereof

<400> SEQUENCE: 20

Asp Cys Ala Tyr Thr Xaa Gly Asn Leu Val Trp Cys Thr
1 5 10

<210> SEQ ID NO 21
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine, or derivative thereof

<400> SEQUENCE: 21

Asp Cys Ser Tyr Thr Xaa Gly Asn Leu Val Trp Cys Thr
1 5 10

<210> SEQ ID NO 22
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine, or derivative thereof

<400> SEQUENCE: 22

Asp Cys Thr Trp Thr Xaa Gly Asn Leu Val Trp Cys Thr
1 5 10

<210> SEQ ID NO 23

<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine, or derivative thereof

<400> SEQUENCE: 23

Asp Cys Thr Tyr His Xaa Gly Asn Leu Val Trp Cys Thr
1 5 10

<210> SEQ ID NO 24
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine, or derivative thereof

<400> SEQUENCE: 24

Asp Cys Thr Tyr Arg Xaa Gly Asn Leu Val Trp Cys Thr
1 5 10

<210> SEQ ID NO 25
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine, or derivative thereof

<400> SEQUENCE: 25

Asp Cys Thr Tyr Ser Xaa Gly Asn Leu Val Trp Cys Thr
1 5 10

<210> SEQ ID NO 26
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine, or derivative thereof

<400> SEQUENCE: 26

Asp Cys Thr Tyr Thr Xaa Gly Asn Leu Val Trp Cys Thr
1 5 10

<210> SEQ ID NO 27
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine, or derivative thereof

<400> SEQUENCE: 27

Asp Cys Thr Tyr Thr Xaa Gly Glu Leu Val Trp Cys Thr
1 5 10

<210> SEQ ID NO 28
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine, or derivative thereof

<400> SEQUENCE: 28

Asp Cys Thr Tyr Thr Xaa Gly Arg Leu Val Trp Cys Thr
1 5 10

<210> SEQ ID NO 29
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine, or derivative thereof

<400> SEQUENCE: 29

Asp Cys Thr Tyr Thr Xaa Gly Asp Leu Val Trp Cys Thr
1 5 10

<210> SEQ ID NO 30
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa is arginine, lysine, leucine, asparagine, or derivative thereof

<400> SEQUENCE: 30

Asp Cys Thr Tyr Thr Xaa Gly Asn Leu Ile Trp Cys Thr
1 5 10

<210> SEQ ID NO 31
<211> LENGTH: 17
<212> TYPE: PRT
<213> ORGANISM: Artificial
<220> FEATURE:
<223> OTHER INFORMATION: Synthetic construct

<400> SEQUENCE: 31

Gly Pro Asp Cys Ala Tyr His Arg Gly Glu Leu Val Trp Cys Thr Phe
1 5 10 15

His

SOLID-PHASE SUPPORT COMPRISING IGG-BINDING PEPTIDE, AND METHOD FOR SEPARATING IGG

SEQUENCE LISTING SUBMISSION VIA EFS-WEB

A computer readable text file, entitled "SequenceListing.txt," created on or about May 16, 2019 with a file size of about 12 kb contains the sequence listing for this application and is hereby incorporated by reference in its entirety.

TECHNICAL FIELD

The present invention relates to a solid-phase support including an IgG-binding peptide; an IgG separation column including the solid-phase support; a kit including the solid-phase support or the column; and a method for purifying IgG using the solid-phase support or the column.

BACKGROUND ART

IgG antibodies are now one of biopharmaceuticals attracting the most attention. In recent years, antibody drugs, particularly IgG antibodies, have been used in the pharmaceutical field, increasingly gaining importance in industrial and pharmaceutical applications thereof. In the purification of antibodies, protein A columns play a central role, and many manufacturers of antibody drugs have adopted purification systems centered on protein A columns.

Several problems, however, have been pointed out for protein A columns. One is contamination of purified antibodies with protein A. Protein A is a protein derived from bacteria and is highly immunogenic after administration to the human body, and endotoxin contamination is a concern. Accordingly, to prevent contamination with unfavorable substances, protein A is required to be highly purified as an affinity ligand used for the purification of pharmaceuticals, such as IgG. This causes an increase in the cost of protein A columns used for the purification of pharmaceuticals. Therefore, development of a new affinity column replacing Protein A is expected.

The present inventors hitherto have reported that IgG can be purified using a peptide ligand including a specific sequence and cyclized by a disulfide bond (Patent Document 1), but the peptide ligand has a problem that its affinity is decreased by repeated washing with an alkaline solution.

CITATION LIST

Patent Literature

Patent Document 1: WO 2013/027796

SUMMARY OF INVENTION

Technical Problem

The present invention provides an IgG-binding peptide which can be used for the purification of IgG and has excellent stability, for example, alkali stability. The present invention also provides a method for purifying IgG using the IgG-binding peptide.

Solution to Problem

The present inventor found that stability of a peptide is remarkably improved by cross-linking sulfide groups in cysteine residues in a peptide by a linker having a specific structure, thereby accomplishing the present invention.

Thus, the present invention includes the following aspects:

(1) A solid-phase support with a peptide immobilized thereon, the peptide being capable of binding to human IgG, wherein the peptide includes an amino acid sequence including from 13 to 17 amino acid residues, the amino acid sequence being represented by Formula I:

$$(X_{1-3})\text{-C-}(X_2)\text{-H-(Xaa1)-G-(Xaa2)-L-V-W-C-}(X_{1-3}) \quad \text{(I)}$$

where X is each independently any amino acid residue other than cysteine,

C is a cysteine residue,

H is a histidine residue,

Xaa1 is an arginine residue, a lysine residue, a leucine residue, or an asparagine residue, or a derivative thereof, G is a glycine residue, Xaa2 is a glutamic acid residue or an asparagine residue, L is a leucine residue, V is a valine residue, and W is a tryptophan residue; and sulfide groups in the two outermost cysteine residues in the peptide are connected via a linker selected from the group consisting of linkers represented by the following formulas:

[Chemical Formula 1]

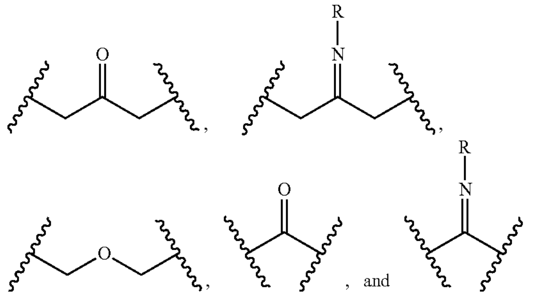

where R is a substituted or unsubstituted C1 to C6 alkyl.

(2) The solid-phase support according to (1), wherein the peptide includes an amino acid sequence including from 13 to 17 amino acid residues, the amino acid sequence being represented by Formula II:

$$(X_{1-3})\text{-C-(Xaa3)-(Xaa4)-H-(Xaa1)-G-(Xaa2)-L-V-W-C-}(X_{1-3}) \quad \text{(II)}$$

where X is each independently any amino acid residue other than cysteine,

C is a cysteine residue,

H is a histidine residue,

Xaa1 is an arginine residue, a lysine residue, a leucine residue, or an asparagine residue, or a derivative thereof, G is a glycine residue, Xaa2 is a glutamic acid residue or an asparagine residue, L is a leucine residue, V is a valine residue, W is a tryptophan residue, Xaa3 is an alanine residue, a serine residue, or a threonine residue, and Xaa4 is a tyrosine residue or a tryptophan residue.

(3) The solid-phase support according to (1) or (2), wherein the peptide includes an amino acid sequence including from 13 to 17 amino acid residues, the amino acid sequence being represented by Formula III:

$(X_{1-3})$-C-A-Y-H-(Xaa1)-G-E-L-V-W-C-$(X_{1-3})$ (III)

where X is each independently any amino acid residue other than cysteine,

C is a cysteine residue,

A is an alanine residue,

Y is a tyrosine residue,

H is a histidine residue,

Xaa1 is an arginine residue, a lysine residue, a leucine residue, or an asparagine residue, or a derivative thereof, G is a glycine residue, E is a glutamic acid residue, L is a leucine residue, V is a valine residue, and W is a tryptophan residue.

(4) The solid-phase support according to any one of (1) to (3), wherein, when the peptide is 17 amino acid residues in length, each amino acid residue at positions 1 to 3 and 15 to 17 from an N-terminus is as follows:

the amino acid residue at position 1=S, G, F, or absent, the amino acid residue at position 2=D, G, A, S, P, homocysteine, or absent, the amino acid residue at position 3=S, D, T, N, E, or R, the amino acid residue at position 15=S, T, or D, the amino acid residue at position 16=H, G, Y, T, N, D, F, homocysteine, or absent, and the amino acid residue at position 17=Y, F, H, M, or absent.

(5) The solid-phase support according to (4), wherein the peptide is selected from the group consisting of the following amino acid sequences of 1) to 14):

```
                                  (SEQ ID NO: 1)
 1) DCAYH(Xaa1)GELVWCT

                                  (SEQ ID NO: 2)
 2) GPDCAYH(Xaa1)GELVWCTFH

                                  (SEQ ID NO: 3)
 3) RCAYH(Xaa1)GELVWCS

                                  (SEQ ID NO: 4)
 4) GPRCAYH(Xaa1)GELVWCSFH

                                  (SEQ ID NO: 5)
 5) SPDCAYH(Xaa1)GELVWCTFH

                                  (SEQ ID NO: 6)
 6) GDDCAYH(Xaa1)GELVWCTFH

                                  (SEQ ID NO: 7)
 7) GPSCAYH(Xaa1)GELVWCTFH

                                  (SEQ ID NO: 8)
 8) GPDCAYH(Xaa1)GELVWCSFH

                                  (SEQ ID NO: 9)
 9) GPDCAYH(Xaa1)GELVWCTHH

                                 (SEQ ID NO: 10)
10) GPDCAYH(Xaa1)GELVWCTFY

                                 (SEQ ID NO: 11)
11) SPDCAYH(Xaa1)GELVWCTFY

                                 (SEQ ID NO: 12)
12) SDDCAYH(Xaa1)GELVWCTFY
```

-continued

```
                                 (SEQ ID NO: 13)
13) RGNCAYH(Xaa1)GQLVWCTYH

                                 (SEQ ID NO: 14)
14) G(Xaa2)DCAYH(Xaa1)GELVWCT(Xaa2)H,
```

with the proviso that Xaa1 is an arginine residue, a lysine residue, a leucine residue, or an asparagine residue, or a derivative thereof; and Xaa2 is homocysteine.

(6) The solid-phase support according to (1) or (2), wherein the peptide includes an amino acid sequence including 13 amino acid residues, the amino acid sequence being represented by Formula IV:

D-C-(Xaa3)-(Xaa4)-H-(Xaa1)-G-(Xaa2)-L-V-W-C-T (IV)

wherein

D is an aspartic acid residue,

C is a cysteine residue,

H is a histidine residue,

Xaa1 is an arginine residue, a lysine residue, a leucine residue, or an asparagine residue, or a derivative thereof, G is a glycine residue, Xaa2 is a glutamic acid residue or an asparagine residue, L is a leucine residue, V is a valine residue, W is a tryptophan residue, T is a threonine residue, Xaa3 is an alanine residue or a threonine residue, and Xaa4 is a tyrosine residue or a tryptophan residue.

(7) The solid-phase support according to (6), wherein the peptide is selected from the group consisting of the following amino acid sequences of 1) to 4):

```
                                 (SEQ ID NO: 15)
1)          DCTYH(Xaa1)GNLVWCT

                                 (SEQ ID NO: 16)
2)          DCAYH(Xaa1)GNLVWCT

                                 (SEQ ID NO: 17)
3)          DCTYH(Xaa1)GELVWCT

                                 (SEQ ID NO: 18)
4)          DCAWH(Xaa1)GELVWCT,
```

with the proviso that Xaa1 is an arginine residue, a lysine residue, a leucine residue, or an asparagine residue, or a derivative thereof.

(8) A solid-phase support with a peptide immobilized thereon, the peptide being capable of binding to human IgG;

wherein the peptide includes an amino acid sequence including 13 amino acid residues, the amino acid sequence being represented by Formula V:

D-C-(Xaa2)-(Xaa3)-(Xaa4)-(Xaa1)-G-(Xaa5)-L-(Xaa6)-W-C-T (V)

where

D is an aspartic acid residue,

C is a cysteine residue,

G is a glycine residue,

L is a leucine residue,

W is a tryptophan residue,

T is a threonine residue,

Xaa1 is an arginine residue, a lysine residue, a leucine residue, or an asparagine residue, or a derivative thereof, Xaa2 is an alanine residue, a serine residue, or a threonine residue, Xaa3 is a tryptophan residue or a tyrosine residue, Xaa4 is a histidine residue, an arginine residue, a serine residue, or a threonine residue, Xaa5 is a glutamic acid residue, an asparagine residue, an arginine residue, or an aspartic acid residue, and Xaa6 is an isoleucine residue or a valine residue; and sulfide groups in the two outermost cysteine residues in the peptide are connected via a linker selected from the group consisting of linkers represented by the following formulas:

[Chemical Formula 2]

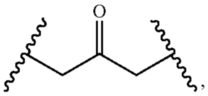, 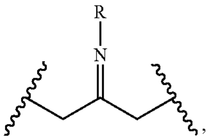, 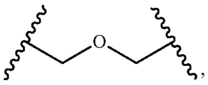, 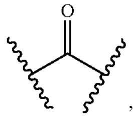, and 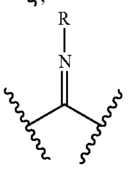

where R is a substituted or unsubstituted C1 to C6 alkyl.

(9) The solid-phase support according to any of (1) to (8), wherein Xaa1 is an arginine residue, a lysine residue or an acylated derivative of lysine, or a leucine residue.

(10) The solid-phase support according to (1), wherein the peptide includes the following amino acid sequence:

GPDCAYHRGELVWCTFH (SEQ ID NO:31).

(11) The solid-phase support according to any one of (1) to (10), wherein the linker is represented by the following formula

[Chemical Formula 3]

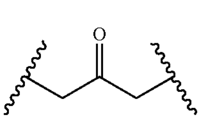 or 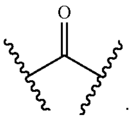.

(12) The solid-phase support according to any one of (1) to (11), wherein the N-terminus of the peptide is PEGylated.

(13) The solid-phase support according to any one of (1) to (12), wherein the C-terminus of the peptide is amidated.

(14) The solid-phase support according to any one of (1) to (13), wherein the peptide is multimerized.

(15) The solid-phase support according to (14), wherein the multimer of the peptide includes a spacer between the peptides.

(16) The solid-phase support according to any one of (1) to (15), including a spacer between the peptide and the solid phase.

(17) An IgG separation column, including the solid-phase support described in any one of (1) to (16).

(18) A kit for purifying IgG, including the solid-phase support described in any one of (1) to (16) or the IgG separation column described in (17).

(19) A method for purifying IgG, including:

binding IgG to the solid-phase support described in any one of (1) to (16) or the IgG separation column described in (17); and eluting the bound IgG to collect the IgG.

The present specification encompasses the disclosure of JP 2016-225483 A which is the basis of priority of the present application.

Advantageous Effects of Invention

The peptide included in the solid-phase support of the present invention has improved stability by cross-linking sulfide groups in cysteine residues by a linker having a specific structure. Accordingly, the IgG binding capacity of the solid-phase support of the present invention is not likely to be diminished due to a process, such as an alkaline washing step, and thus the solid-phase support of the present invention can be used for an efficient purification of IgG.

DESCRIPTION OF EMBODIMENTS

Solid-Phase Support Including IgG-Binding Peptide

Figure 1:
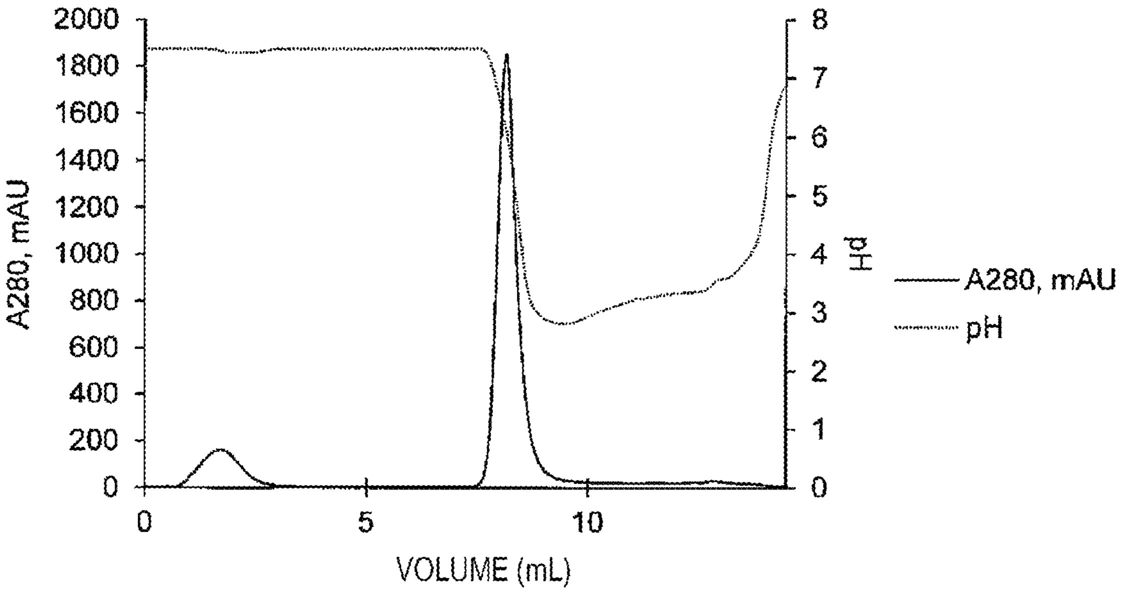
FIG. 1 illustrates a result of a case where human serum-derived γ-globulin (Wako) was adsorbed to a column with immobilized peptide prepared in Example 3 and eluted with an acidic elution solution (20 mM citric acid, pH 2.5). The horizontal axis represents the volume of the elution liquid and the vertical axis represents the peptide concentration measured by absorbance at 280 nm.

In one aspect, an embodiment of the present invention relates to a solid-phase support including an IgG-binding peptide. Examples of the "solid-phase support" in the present specification include, but are not limited to, inorganic supports, such as glass beads and silica gel; organic supports composed of a synthetic polymer, such as cross-linked polyvinyl alcohol, cross-linked polyacrylate, cross-linked polyacrylamide, and cross-linked polystyrene; and polysaccharide, such as crystalline cellulose, cross-linked cellulose, cross-linked agarose, and cross-linked dextran; as well as composite supports obtained from combinations thereof, such as organic-organic and organic-inorganic supports. Among them, hydrophilic supports are preferred due to their relatively low non-specific adsorption and good selectivity for the IgG-binding peptide. Hydrophilic supports herein refer to supports with a water contact angle of 60° or less when a compound forming the support is produced into a flat plate shape. Representative examples of such supports include those composed of polysaccharide, such as cellulose, chitosan, and dextran; polyvinyl alcohol; a saponified ethylene-vinyl acetate copolymer; polyacrylamide; polyacrylic acid; polymethacrylic acid; polymethyl methacrylate; polyacrylic acid-grafted polyethylene; polyacrylamide-grafted polyethylene; and glass.

The solid-phase support may be in any form, such as beads, fibers, particles, membranes (including hollow fibers), and gels; and a solid-phase support in any form can be selected. Solid-phase supports in a bead form are particularly preferably used for ease of preparing a support having a specific exclusion limit molecular weight. Solid-phase supports in a bead form having an average particle size ranging from 10 to 2500 μm are easy to use; and in particular, those having an average particle size ranging from 25 μm to 800 μm are preferred for ease of immobilization reaction of the IgG-binding peptide. Specifically, examples of the solid-phase support include magnetic beads, glass beads, polystyrene beads, silica gel beads, and polysaccharide beads.

In addition, presence of a functional group, which can be used for the immobilization reaction of the IgG-binding peptide, on the surface of the solid-phase support is advantageous for immobilizing the IgG-binding peptide. Representative examples of these functional groups include a hydroxy group, an amino group, an aldehyde group, a carboxyl group, a thiol group, a silanol group, an epoxy group, a succinimide group, an N-hydroxysuccinimide group, an acid anhydride group, and an iodoacetyl group.

A commercially available solid-phase support can be also used. A commercially available products can be exemplified by GCL2000 and GC700, which are porous cellulose gels; Sephacryl S-1000, obtained by covalently cross-linking an allyl dextran and methylenebisacrylamide; Toyopearl, an acrylate-based support; Sepharose CL4B, an agarose-based cross-linked support; Eupergit C250L, a polymethacrylamide activated with epoxy groups; and an NHS-activated prepacked column containing a sepharose support activated with NHS groups. The present embodiment, however, is not limited to only these supports or activated supports.

The solid-phase supports described above may be each used alone or in a mixture of any two or more types. In addition, in view of its intended use and method, the solid-phase support desirably has a large surface area and thus a large number of pores with a suitable size; that is, the solid-phase support is preferably porous.

Preferably, the IgG-binding peptide described in the present specification is immobilized on the solid-phase support. The peptide can be immobilized by a method known to those skilled in the art, for example, by physical adsorption method, covalent bonding method, and ionic bonding method. It is preferable to achieve the immobilization, for example, by covalently binding the N-terminal amino group of the IgG-binding peptide to the solid-phase support directly or via a spacer. It is more preferable to immobilize the peptide via a hydrophilic spacer in order to enhance separation efficiency by reducing steric hindrance of the IgG-binding peptide, and in order to suppress non-specific binding. The hydrophilic spacer is not particularly limited, but it is preferable to use, for example, a derivative of a polyalkylene oxide, which has both terminals substituted with functional groups, such as a carboxyl group, an amino group, an aldehyde group, and an epoxy group.

A method and conditions for immobilizing the IgG-binding peptide to be introduced to the solid-phase support and an organic compound to be used as the spacer are not particularly limited, but they are exemplified by methods commonly employed to immobilize a protein and a peptide on a support. One example is a method including: subjecting a support to a reaction with a compound containing an amino group, a compound containing an N-hydroxysuccinimidyl group, cyanogen bromide, epichlorohydrin, diglycidyl ether, tosyl chloride, tresyl chloride, hydrazine, or the like, to activate the support (by transforming a functional group into a group that is more reactive with an IgG-binding peptide than the functional group the support originally has); and then subjecting the support to a reaction with an IgG-binding peptide to immobilize the peptide thereto. Another immobilization method includes adding a condensation reagent, such as carbodiimide, or a reagent having a plurality of functional groups in a molecule, such as glutaraldehyde, into a system in which a support and an IgG-binding peptide are present, to condense or cross-link them, thereby immobilizing them. It is more preferable, however, to utilize an immobilization method where the IgG-binding peptide is not easily released from the solid-phase support during sterilization or use of the solid-phase support.

The solid-phase support including the IgG-binding peptide described in the present specification can be loaded into a chromatography column, and the like, and used to purify or separate human IgG.

The IgG-binding peptide included in the solid-phase support of an embodiment of the present invention will be described in detail below.

"IgG" used in the present specification refers to IgG of mammals, for example, primates, such as humans and chimpanzees; experimental animals, such as rats, mice, and rabbits; livestock animals, such as pigs, cows, horses, sheep, and goats; and pet animals, such as dogs and cats; preferably IgG of human (IgG1, IgG2, IgG3, or IgG4). IgG in the present specification is more preferably human IgG1, IgG2, or IgG4, or rabbit IgG, and particularly preferably human IgG1, IgG2, or IgG4.

In one aspect, the IgG-binding peptide that may be included in the solid-phase support of an embodiment of the present invention includes an amino acid sequence including from 13 to 17 amino acid residues that is represented by Formula I:

$$(X_{1-3})\text{-C-}(X_2)\text{-H-(Xaa1)-G-(Xaa2)-L-V-W-C-}(X_{1-3}) \quad \text{(I)}$$

where X is each independently any amino acid residue other than cysteine,

C is a cysteine residue,

H is a histidine residue,

Xaa1 is an arginine residue, a lysine residue, a leucine residue, or an asparagine residue, or a derivative thereof, G is a glycine residue, Xaa2 is a glutamic acid residue or an asparagine residue, L is a leucine residue, V is a valine residue, and W is a tryptophan residue; and sulfide groups in the two outermost cysteine residues in the peptide are connected via a linker selected from the group consisting of linkers represented by the following formulas:

[Chemical Formula 4]

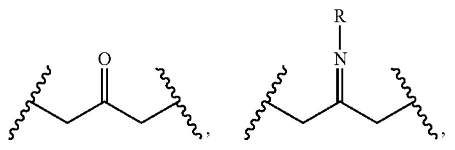

-continued

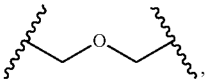, 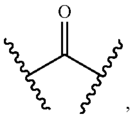, and 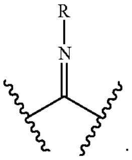.

In the above formula, the denotation of $X_{1-3}$ at the N-terminus or C-terminus means from one to three consecutive amino acid residues X, each independently representing any amino acid residue other than cysteine (C or Cys). Although the amino acid residues of this moiety are the same or different, this moiety preferably includes a sequence in which all three residues are not identical. Similarly, $X_2$ also means two consecutive amino acid residues X, each independently representing any amino acid residue other than cysteine (C or Cys). Although the amino acid residues of this moiety are the same or different, this moiety preferably includes a sequence in which the two consecutive amino acid residues are not the same.

Peptides represented by Formulas I' and I'', which further specify the amino acid residues X in the amino acid sequence of the peptide of Formula I, are shown below.

That is, the peptide represented by Formula I' includes an amino acid sequence including from 13 to 17 amino acid residues that is represented by $(X_{1-3})$-C-$(X_1)$-Y-H-(Xaa1)-G-N-L-V-W-C-$(X_{1-3})$ (I')

where X is each independently any amino acid residue other than cysteine,

C is a cysteine residue,

Y is a tyrosine residue,

H is a histidine residue,

Xaa1 is an arginine residue, a lysine residue, a leucine residue, or an asparagine residue, or a derivative thereof, G is a glycine residue, N is an asparagine residue, L is a leucine residue, V is a valine residue, and W is a tryptophan residue.

The peptide represented by Formula I'' includes an amino acid sequence including 13 to 17 amino acid residues that is represented by $(X_{1-3})$-C-A-$(X_1)$-H-(Xaa1)-G-E-L-V-W-C-$(X_{1-3})$ (I'')

where X is each independently any amino acid residue other than cysteine,

C is a cysteine residue,

A is an alanine residue,

H is a histidine residue,

Xaa1 is an arginine residue, a lysine residue, a leucine residue, or an asparagine residue, or a derivative thereof, G is a glycine residue, E is a glutamic acid residue, L is a leucine residue, V is a valine residue, and W is a tryptophan residue.

Further, a peptide represented by Formula II, which further specifies the amino acid residues X in the amino acid sequence of the peptide of Formula I, is shown below.

That is, the peptide represented by Formula II includes an amino acid sequence including from 13 to 17 amino acid residues that is represented by $(X_{1-3})$-C-(Xaa3)-(Xaa4)-H-(Xaa1)-G-(Xaa2)-L-V-W-C-$(X_{1-3})$ (II)

where X is each independently any amino acid residue other than cysteine,

C is a cysteine residue,

H is a histidine residue,

Xaa1 is an arginine residue, a lysine residue, a leucine residue, or an asparagine residue, or a derivative thereof, G is a glycine residue, Xaa2 is a glutamic acid residue or an asparagine residue, L is a leucine residue, V is a valine residue, W is a tryptophan residue, Xaa3 is an alanine residue, a serine residue, or a threonine residue, and Xaa4 is a tyrosine residue or a tryptophan residue.

When the amino acid sequences of the peptides of Formulas I', I'', and II above include 17 amino acid residues, the amino acid residues X at positions 1 and 2 as well as 16 and 17 from the N-terminus may be absent, and the resulting peptides will include 13 amino acids in length.

"When . . . include(s) 17 amino acid residues" as used in the present specification is a phrase used for the sake of convenience to number 17 amino acid residues, which are the longest possible amino acid length for the peptide of Formula I, from position 1 at the N-terminus to position 17 in order when the amino acid residues of the peptide are designated by amino acid numbers.

Furthermore, a peptide represented by Formulas III, which further specifies the amino acid residues X in the amino acid sequence of the peptide of Formula I, is shown below.

That is, the peptide represented by Formula III includes an amino acid sequence including from 13 to 17 amino acid residues that is represented by $(X_{1-3})$-C-A-Y-H-(Xaa1)-G-E-L-V-W-C-$(X_{1-3})$ (III)

where X is each independently any amino acid residue other than cysteine,

C is a cysteine residue,

A is an alanine residue,

Y is a tyrosine residue,

H is a histidine residue,

Xaa1 is an arginine residue, a lysine residue, a leucine residue, or an asparagine residue, or a derivative thereof, G is a glycine residue, E is a glutamic acid residue, L is a leucine residue, V is a valine residue, and W is a tryptophan residue.

When the amino acid sequence of the peptide of Formula III above includes 17 amino acid residues, the amino acid residues X at positions 1 and 2 as well as 16 and 17 from the N-terminus may be absent, and the resulting peptide may include 13 amino acids in length.

In addition, the amino acid residues other than cysteine (C) in the amino acid sequences of the peptide of each formula above, i.e., when the peptide includes 17 amino acid residues, each amino acid residue at positions 1 to 3, 5, 6, and 15 to 17 from the N-terminus is preferably selected from the following amino acid residues: wherein each upper case alphabetic character denotes the amino acid single letter code, the amino acid residue at position 1=S, G, F, or absent, the amino acid residue at position 2=D, G, A, S, P, homocysteine, or absent, the amino acid residue at position 3=S, D, T, N, E, or R, the amino acid residue at position 15=S, T, or D, the amino acid residue at position 16=H, G, Y, T, N, D, F, homocysteine, or absent, the amino acid residue at position 17=Y, F, H, M, or absent, the amino acid residue at position 5=A or T, the amino acid residue at position 6=Y or W.

Further, a peptide represented by Formula IV, which further specifies the amino acid residues X in the amino acid sequence of the peptide of Formula I, is shown below.

That is, the peptide represented by Formula IV includes an amino acid sequence including 13 amino acid residues that is represented by D-C-(Xaa3)-(Xaa4)-H-(Xaa1)-G-(Xaa2)-L-V-W-C-T (IV)

wherein

D is an aspartic acid residue,

C is a cysteine residue,

H is a histidine residue,

Xaa1 is an arginine residue, a lysine residue, a leucine residue, or an asparagine residue, or a derivative thereof, G is a glycine residue, Xaa2 is a glutamic acid residue or an asparagine residue, L is a leucine residue, V is a valine residue, W is a tryptophan residue, T is a threonine residue, Xaa3 is an alanine residue or a threonine residue, and Xaa4 is a tyrosine residue or a tryptophan residue.

Some specific examples of the peptide of Formula I are listed in the following 1) to 18), but needless to say, the peptide is not limited thereto:

```
                                  (SEQ ID NO: 1)
 1) DCAYH(Xaa1)GELVWCT,

                                  (SEQ ID NO: 2)
 2) GPDCAYH(Xaa1)GELVWCTFH,

                                  (SEQ ID NO: 3)
 3) RCAYH(Xaa1)GELVWCS,

                                  (SEQ ID NO: 4)
 4) GPRCAYH(Xaa1)GELVWCSFH,

                                  (SEQ ID NO: 5)
 5) SPDCAYH(Xaa1)GELVWCTFH,

                                  (SEQ ID NO: 6)
 6) GDDCAYH(Xaa1)GELVWCTFH,

                                  (SEQ ID NO: 7)
 7) GPSCAYH(Xaa1)GELVWCTFH,

                                  (SEQ ID NO: 8)
 8) GPDCAYH(Xaa1)GELVWCSFH,

                                  (SEQ ID NO: 9)
 9) GPDCAYH(Xaa1)GELVWCTHH,

                                 (SEQ ID NO: 10)
10) GPDCAYH(Xaa1)GELVWCTFY,

                                 (SEQ ID NO: 11)
11) SPDCAYH(Xaa1)GELVWCTFY,

                                 (SEQ ID NO: 12)
12) SDDCAYH(Xaa1)GELVWCTFY,

                                 (SEQ ID NO: 13)
13) RGNCAYH(Xaa1)GQLVWCTYH,

                                 (SEQ ID NO: 14)
14) G(Xaa2)DCAYH(Xaa1)GELVWCT(Xaa2)H,
```

-continued

```
                                 (SEQ ID NO: 15)
15) DCTYH(Xaa1)GNLVWCT,

                                 (SEQ ID NO: 16)
16) DCAYH(Xaa1)GNLVWCT,

                                 (SEQ ID NO: 17)
17) DCTYH(Xaa1)GELVWCT,
and

                                 (SEQ ID NO: 18)
18) DCAWH(Xaa1)GELVWCT,
```

wherein Xaa1 is an arginine residue, a lysine residue, a leucine residue, or an asparagine residue, or a derivative thereof; Xaa2 is homocysteine, and a disulfide bond is preferably formed between homocysteines.

Preferred specific examples of the peptide of Formula I include:

1) DCAYH(Xaa1)GELVWCT (SEQ ID NO:1, wherein Xaa1 is R),

2) GPDCAYH(Xaa1)GELVWCTFH (SEQ ID NO:2, wherein Xaa1 is R, L, K, or acetylated lysine), and 4) GPRCAYH(Xaa1)GELVWCSFH (SEQ ID NO:4, wherein Xaa1 is R); and particularly preferred examples include GPDCAYHRGELVWCTFH (SEQ ID NO:31).

Further, in one aspect, the IgG-binding peptide described in the present specification includes an amino acid sequence including 13 amino acid residues as a primary structure in a broad sense, the amino acid sequence being represented by Formula V:

D-C-(Xaa2)-(Xaa3)-(Xaa4)-(Xaa1)-G-(Xaa5)-L-(Xaa6)-W-C-T (V)

where

D is an aspartic acid residue,

C is a cysteine residue,

G is a glycine residue,

L is a leucine residue,

W is a tryptophan residue,

T is a threonine residue,

Xaa1 is an arginine residue, a lysine residue, a leucine residue, or an asparagine residue, or a derivative thereof, Xaa2 is an alanine residue, a serine residue, or a threonine residue, Xaa3 is a tryptophan residue or a tyrosine residue, Xaa4 is a histidine residue, an arginine residue, a serine residue, or a threonine residue, Xaa5 is a glutamic acid residue, an asparagine residue, an arginine residue, or an aspartic acid residue, and Xaa6 is an isoleucine residue or a valine residue; and sulfide groups in the two outermost cysteine residues in the peptide are connected via a linker selected from the group consisting of linkers represented by the following formulas:

[Chemical Formula 5]

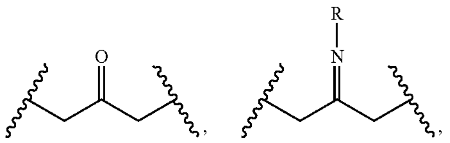

-continued

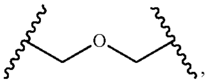, 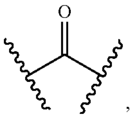, and 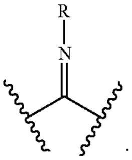.

Some specific examples of the peptide of Formula V are listed in the following 19) to 30), but needless to say, the peptide is not limited thereto:

```
                                  (SEQ ID NO: 19)
19)          DCTYT(Xaa1)GNLVWCT,

                                  (SEQ ID NO: 20)
20)          DCAYT(Xaa1)GNLVWCT,

                                  (SEQ ID NO: 21)
21)          DCSYT(Xaa1)GNLVWCT,

                                  (SEQ ID NO: 22)
22)          DCTWT(Xaa1)GNLVWCT,

                                  (SEQ ID NO: 23)
23)          DCTYH(Xaa1)GNLVWCT,

                                  (SEQ ID NO: 24)
24)          DCTYR(Xaa1)GNLVWCT,

                                  (SEQ ID NO: 25)
25)          DCTYS(Xaa1)GNLVWCT,

                                  (SEQ ID NO: 26)
26)          DCTYT(Xaa1)GNLVWCT,

                                  (SEQ ID NO: 27)
27)          DCTYT(Xaa1)GELVWCT,

                                  (SEQ ID NO: 28)
28)          DCTYT(Xaa1)GRLVWCT,

                                  (SEQ ID NO: 29)
29)          DCTYT(Xaa1)GDLVWCT,
and

                                  (SEQ ID NO: 30)
30)          DCTYT(Xaa1)GNLIWCT,
```

where Xaa1 is an arginine residue, a lysine residue, a leucine residue, or an asparagine residue, or a derivative thereof.

As described above, in the IgG-binding peptide described in the present specification, Xaa1 is an arginine residue, a lysine residue, a leucine residue, or an asparagine residue, or a derivative thereof; preferably an arginine residue, a lysine residue or a derivative of a lysine residue, a leucine residue, or an asparagine residue; and more preferably an arginine residue, a lysine residue or a derivative of a lysine residue, or a leucine residue. In the present specification, the type of the derivative is not particularly limited, but examples thereof include acylated derivatives, such as an acetyl group or a propynyl group (acylated derivatives are represented by a general formula: R-CO-, wherein R is a hydrocarbon, preferably an alkyl having from 1 to 6 carbons). Examples of the derivative include a derivative of a lysine residue where an ε-amino group of the lysine residue is acylated, for example acetylated.

As described above, the IgG-binding peptide described in the present specification has at least two cysteine (C) residues positioned separately from each other in each amino acid sequence, and sulfide groups of the cysteine residues are connected via a linker selected from the group consisting of linkers represented by the following formulas:

[Chemical Formula 6]

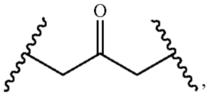, 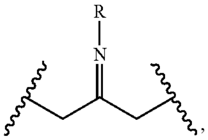,

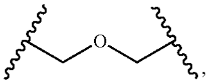, 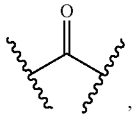, and 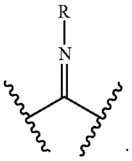.

The linker in the IgG-binding peptide is preferably a linker represented by

[Chemical Formula 7]

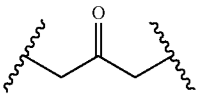 or 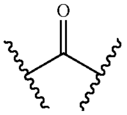, and more preferably a linker represented by

[Chemical Formula 8]

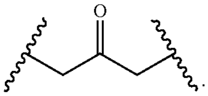.

R in the linker in the IgG-binding peptide is a substituted or unsubstituted alkyl, and preferably a substituted or unsubstituted C1 to C6 alkyl, i.e., a methyl group, an ethyl group, a propyl group, a butyl group, a pentyl group, or a hexyl group. The substituted group of R is not particularly limited, but it may be, for example, a hydroxy group, a (mono or poly) ethylene oxide group, a carboxyl group, an alkoxy group, an acyl group, an alkyl group, an amide group, an ester group, a halogen group (F, Cl, Br, or I), or combinations thereof. In addition, the wavy line portions mean bonding portions with the sulfide groups. As compared with a common disulfide bond, the linker is superior in stability, for example, alkali resistance or reduction reaction resistance, and preferably in alkali resistance.

A method for preparing the peptide having the linker is not particularly limited. For example, a peptide having a linker represented by the following formula:

[Chemical Formula 9]

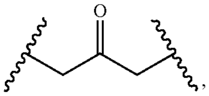, 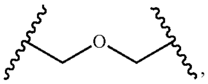, and

-continued

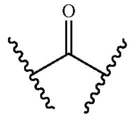

can be obtained, for example, by a method including mixing a peptide containing two cysteine residues, and a compound having, at the wavy line portions of the linker, reactive functional groups (for example, halogen groups and imidazole groups) which are to be involved in the cross-linking reaction, for example, under acidic conditions.

Furthermore, a peptide connected via a linker represented by

[Chemical Formula 10]

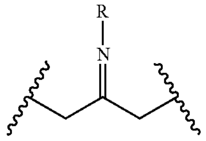

or

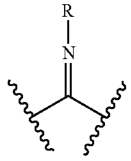

can be obtained by subjecting a peptide having the above carbonyl group to a reaction with a primary amine ($RNH_2$), where R means the same as described above.

The halogen groups in the compound above are selected preferably from the group consisting of F, Cl, Br, and I; and more preferably from the group consisting of Cl, Br, and I. The halogen groups are preferably the same to each other, and more preferably all the halogen groups are Cl.

The conditions for the mixing step in the preparation method are not particularly limited as long as they can proceed the linking reaction between and the cysteine residues of the peptide to occur. For example, the reaction can be carried out by mixing the peptide and the compound above in a suitable buffer at room temperature (for example, about 15° C. to 30° C.) or at low temperature. The mixing step may be carried out by adding an appropriate amount of a base (or an alkali) that promotes the linking reaction, for example, a weak basic inorganic or organic compound (for example, guanidium chloride, sodium bicarbonate, and diethylamine).

A mixing ratio of the peptide and the compound in the mixing step of the preparation method is not particularly limited. A molar ratio of the peptide and the compound can be, for example, from 1:0.2 to 1:10, preferably from 1:0.5 to 1:5 or from 1:1 to 1:2.

A mixing time (reaction time) of the mixing step is not limited as long as the linking reaction can occur between the cysteine residues in the peptide, but it can be, for example, from 1 min to 5 hours, and preferably from 10 min to 2 hours or from 15 min to 1 hour.

The method, as necessary, may further include separating impurities, such as, for example, an unreacted peptide or an unreacted compound, from the mixture after the mixing step, to purify a peptide of which cysteine residues are linked together. The step can be carried out by a known method in the art, for example, chromatography, such as gel filtration chromatography, ion-exchange column chromatography, affinity chromatography, reverse-phase column chromatography, and HPLC.

In addition, the IgG-binding peptide described in the present specification may be modified, for example, by N-terminal PEGylation (polyethylene glycol addition) and C-terminal amidation, for example, to improve stability thereof. The number of PEG molecules for the PEGylation is not particularly limited, and, for example, from 1 to 50 molecules, from 1 to 20 molecules, from 2 to 10 molecules, from 2 to 6 molecules, or 4 molecules of PEG can be added.

Furthermore, the IgG-binding peptide described in the present specification may be multimerized. In the present specification, "multimerization" of the IgG-binding peptide means that two or more molecules of the IgG-binding peptide are linked via a covalent bond. The multimer of the IgG-binding peptide may be, for example, from a dimer to a hexamer, from a dimer to a pentamer, from a dimer to a tetramer, from a dimer to a trimer, and preferably a dimer.

The multimer of the peptide may include a spacer between the peptides. The multimerization can be achieved by a method known to those skilled in the art, for example, by linking N-terminal amino groups of two or more molecules of the IgG-binding peptide via a spacer. The type of the spacer is not particularly limited, but examples thereof include an amino acid such as aspartic acid and glutamic acid, which have carboxyl groups at both termini; and a derivative of a polyalkylene oxide, which is substituted at both termini with functional groups, such as a carboxyl group, an aldehyde group, an epoxy group, and an N-hydroxysuccinimidyl group.

The IgG-binding peptide described in the present specification has binding affinity for human IgG which may be at least about 10 times, preferably at least about 50 times, and more preferably at least about 200 times as high as that for other human immunoglobulins (IgA, IgE, and IgM). The dissociation constant (Kd) for binding between the peptide described in the present specification and human IgG can be determined by surface plasmon resonance spectral analysis (for example, using a BIACORE system), and Kd is, for example, less than $1\times10^{-1}$ M, less than $1\times10^{-3}$ M, preferably less than $1\times10^{-4}$ M, and more preferably less than $1\times10^{-5}$ M. The IgG-binding peptide described in the present specification can bind to the Fc domain of IgG.

The peptide described in the present specification can be produced by a peptide synthesis method, such as commonly used liquid phase peptide synthesis and solid phase peptide synthesis, and also by peptide synthesis with an automated peptide synthesizer (Kelley et al., Genetics Engineering Principles and Methods, Setlow, J. K. eds., Plenum Press NY. (1990) Vol. 12, p. 1-19; Stewart et al., Solid-Phase Peptide Synthesis (1989) W.H. Freeman Co.; Houghten, Proc. Natl. Acad. Sci. USA (1985) 82:p. 5132; "Shinseikagakujikken kouza 1, tanpakushitsu IV (literally translated as: New Biochemical Experiment Lecture 1 Protein IV)" (1992), edited by The Japanese Biochemical Society, Tokyo Kagaku Dojin). Alternatively, the peptide may be produced by a method, such as a genetic recombination method and a phage display method, using a nucleic acid encoding the peptide described in the present specification. For example, the target peptide can be produced by incorporating DNA encoding the amino acid sequence of the peptide described in the present specification into an expression vector, introducing the resulting vector into a host cell, and then culturing the host cell. The peptide thus produced can be collected or purified by an ordinary method, for example, chromatography, such as gel filtration chromatography, ion-exchange column chromatography, affinity chromatography, reverse-phase column chromatography, and HPLC; ammonium sulphate fractionation, ultrafiltration, and an immunoadsorption method.

To synthesize the peptide, amino acids are prepared by protecting functional groups of each amino acid (whether natural or unnatural) other than the α-amino group and the α-carboxyl group to be bound, and then the α-amino group and the α-carboxyl group of each amino acid are subjected to a reaction to form a peptide bond therebetween. Typically, the carboxyl group of an amino acid residue positioned at the C-terminus of the peptide is bound to a solid phase in advance via a suitable spacer or linker. The protecting group at the amino terminus of the dipeptide thus obtained is selectively removed, and a peptide bond with the α-carboxyl group of the next amino acid is formed. Such an operation is continuously carried out to produce a peptide having protected side groups, and finally, all the protecting groups are removed, and the peptide is detached from the solid phase. Types of the protecting group, a protection method, and a peptide binding method are detailed in the above documents.

Production by a genetic recombination method may include, for example, inserting DNA that encodes the peptide described in the present specification into a suitable expression vector, introducing the resulting vector into a suitable host cell, culturing the cell, and collecting the target peptide from the inside of the cell or from the extracellular fluid. Examples of the vector include, but are not limited to, a vector, such as a plasmid, a phage, a cosmid, a phagemid, and a virus. Examples of the plasmid vector include, but are not limited to, an *E. coli*-derived plasmid (such as pET22b (+), pBR322, pBR325, pUC118, pUC119, pUC18, pUC19, and pBluescript), a *Bacillus subtilis*-derived plasmid (such as pUB110 and pTPS), and a yeast-derived plasmid (such as YEp13 and YCp50). Examples of the phage vector include, but are not limited to, a T7 phage display vector (such as T7Select10-3b, T7Select1-1b, T7Select1-2a, T7Select1-2b, and T7Select1-2c (Novagen)) and a λ phage vector (such as Charon4A, Charon21A, EMBL3, EMBL4, λgt10, λgt11, λZAP, and λZAPII). Examples of the virus vector include, but are not limited to, an animal virus, such as a retrovirus, an adenovirus, an adeno-associated virus, a vaccinia virus, and Sendai virus; and an insect virus, such as a baculovirus. Examples of the cosmid vector include, but are not limited to, Lorist 6, Charomid 9-20, and Charomid 9-42. Examples of a known phagemid vector include, but are not limited to, pSKAN, pBluescript, pBK, and pComb3H. A vector can include, for example, a regulatory sequence so as to enable the expression of the target DNA, a selection marker to select a vector containing the target DNA, and a multicloning site to insert the target DNA. Such a regulatory sequence includes, for example, a promoter, an enhancer, a terminator, an S-D sequence or a ribosome binding site, a replication origin, and a poly A site. In addition, as the selection marker, for example, an ampicillin resistant gene, a neomycin resistant gene, a kanamycin resistant gene, and a dihydrofolate reductase gene can be used. The host cell into which the vector is to be introduced is, for example, a bacterium, such as *E. coli* and *Bacillus subtilis*; a yeast cell; an insect cell; an animal cell (such as a mammalian cell), and a plant cell. Examples of transformation or transfection into these cells include a calcium phosphate method, an electroporation method, a lipofection method, a particle bombardment method, and a PEG method. The transformed cells are cultured in accordance with a common method used for culturing host organisms. For example, a culture medium for microorganisms, such as *E. coli* and yeast cells, contains a substance, such as a carbon source, a nitrogen source, and inorganic salts, that can be utilized by the host microorganisms. To simplify the collection of the peptide described in the present specification, it is preferable to allow the host organisms to secrete the peptide produced by expression to the outside of the cell. This can be achieved by binding a DNA that encodes a peptide sequence enabling the secretion of the peptide from the cell to the 5'-terminal side of the DNA that encodes the target peptide. A fusion peptide that has migrated to the cell membrane is cleaved by signal peptidase, and thus the target peptide is secreted and released into the medium. Alternatively, it is also possible to collect the target peptide that has accumulated inside the cell. In this case, the cell is physically or chemically destroyed, and the target peptide is collected using a protein purification technique.

IgG Separation Column and Kit for IgG Purification

In one aspect, an embodiment of the present invention relates to a column for separating an IgG, preferably a human IgG, that includes the solid-phase support including the IgG-binding peptide.

The IgG separation column encompasses a column, such as a chromatography column and a high-performance liquid chromatography (HPLC) column, for purification or separation of IgG. The size of the column is not particularly limited, and it can be varied depending on, for example, the intended use, such as for analysis, purification, or fractionation; the amount of a sample to be applied (loaded) or injected, and the length or the inner diameter of the column. Also, the column may be made of a material commonly used for a column, such as metal, plastic, and glass.

The column can be produced by densely filling a column with the solid-phase support of an embodiment of the present invention (which may be in either dry or wet state).

In one aspect, an embodiment of the present invention relates to a kit for purifying IgG, preferably human IgG, that includes the solid-phase support including the IgG-binding peptide.

The kit of an embodiment of the present invention may include at least one of: a manual for use describing analytical procedures and purification procedures for human IgG, a reagent and a buffer necessary for purification, or a column to be filled with the solid-phase support.

IgG Purification Method

In one aspect, an embodiment of the present invention relates to a method for purifying IgG, preferably human IgG, including: binding IgG to the solid-phase support or the IgG separation column; and eluting the bound IgG to collect the IgG.

The binding step can be carried out by a method known to those skilled in the art. For example, the solid-phase support or the IgG separation column are equilibrated with a suitable buffer, and then a liquid containing IgG is applied thereto at low temperature from 0° C. to room temperature, preferably from 0° C. to about 10° C., more preferably at about 4° C., to bind the IgG to the peptide on the solid-phase support. For example, to separate IgG in serum, the binding step can be carried out by applying a liquid containing serum and IgG to the column, using a buffer having a pH in the neutral range, for example, pH from 6.0 to 7.5.

The elution step can be also carried out by a method known to those skilled in the art. For example, the IgG may be eluted by feeding a buffer having a pH in the acidic range, for example, pH from 2 to 4 (for example, 0.2 M glycine-HCl buffer or 20 mM citrate buffer, containing 0.3 M NaCl, from pH 3.5 to pH 2.5), through the column, or by competitive elution using the IgG-binding peptide. In particular, it is preferable to carry out the elution with acid from the perspective of cost. In this case, the solid-phase support or the column can be regenerated and reused in the binding step by washing the support or the column with an alkaline solution, such as a sodium hydroxide solution, a potassium hydroxide solution, and a potassium hydroxide solution (for example, 0.1 M sodium hydroxide solution). The degree of alkalinity of the solution will be easily determined by those skilled in the art. Accordingly, the method of an embodiment of the present invention can optionally include regenerating the solid-phase support or the column by washing with an alkaline solution.

Whether IgG is collected can be determined, for example, by identification of molecular weight by electrophoresis, and optionally subsequent Western blotting using an anti-IgG antibody. For example, the electrophoresis may be carried out by SDS-PAGE using a 5 to 20% acrylamide gradient gel, and Western blotting can be carried out by transferring proteins after electrophoresis to a PVDF membrane, followed by blocking with skimmed milk, and then detecting the IgG with a goat anti-IgG a chain antibody and an HRP-labeled mouse anti-goat IgG antibody.

The method of an embodiment of the present invention is useful for obtaining an IgG-rich fraction in a step of purifying IgG from an IgG-containing product produced by various methods. Thus, it is preferable to use the method of an embodiment of the present invention in column chromatography, such as affinity chromatography and HPLC. For purification of IgG, in addition to such chromatography, commonly used protein purification techniques, for example, chromatography, such as gel filtration chromatography, ion-exchange column chromatography, and reverse-phase column chromatography; ammonium sulphate fractionation; and ultrafiltration can be combined as appropriate.

Embodiments of the present invention will be further specifically described with reference to the following examples, the scope of the present invention is, however, not limited by these examples.

EXAMPLES

Example 1: Preparation of IgG-Binding Peptide and Measurement of Binding Affinity The following six IgG-binding peptides blocked at the N-terminus with biotinylated PEG4 were synthesized by Fmoc solid-phase synthesis in accordance with an ordinary method:

DCAYH(Xaa1)GELVWCT (SEQ ID NO:1, wherein Xaa1 was arginine and the C-terminus was amidated);

GPRCAYH(Xaa1)GELVWCSFH (SEQ ID NO:4, wherein Xaa1 was arginine and the C-terminus was amidated);

GPDCAYH(Xaa1)GELVWCTFH (SEQ ID NO:2, wherein Xaa1 was arginine and the C-terminus was amidated); GPDCAYH(Xaa1)GELVWCTFH (SEQ ID NO:2, wherein Xaa1 was leucine, and the C-terminus was amidated);

GPDCAYH(Xaa1)GELVWCTFH (SEQ ID NO:2, wherein Xaa1 was lysine, and the C-terminus was amidated); and GPDCAYH(Xaa1)GELVWCTFH (SEQ ID NO:2, wherein Xaa1 was acetylated lysine, and the C-terminus was amidated).

After a protecting group was removed, an intramolecular S-S bond was formed in an aqueous solution having a pH of 8.5 under oxidative conditions, and a peptide having the intramolecular S-S bond was purified by reverse-phase HPLC using a gradient elution with 10% to 60% acetonitrile containing 0.1% TFA at a flow rate of 1.0 mL/min.

Affinity analysis of the purified IgG-binding peptide was carried out according to the following method. Equal amounts of 0.4 M 1-ethyl-3-(3-dimethylaminopropyl)-carbodiimide (EDC) and 0.1 M sulfo-N-hydroxysuccinimide (sulfo-NHS) were mixed and injected onto a CMS sensor chip, which was set in BIAcoreT200 (GE healthcare), at a flow rate of 10 μL/mL for 7 min to activate the sensor chip, and then the IgG was immobilized on the sensor chip under conditions of pH 4.0 (10 mM Na acetate) so as to give an immobilized amount of 4000 to 5000 in RU value. The binding reaction was monitored by injecting the peptide in a concentration from 10 nM to 2 μM at a flow rate of 50 μL/mL for 180 sec while using an HBS-EP buffer (0.01 M HEPES, 0.15 M NaCl, 0.005% TWEEN 20, 3 mM EDTA, pH 7.0), and then the dissociation reaction was measured by washing with the buffer for 600 sec. Binding parameters were analyzed using BIAevalution T100 software.

Results of the affinity measurement are shown in Table 1 below. Results in Table 1 show that all the peptides can bind to IgG and thus can be used for purification of an antibody.

TABLE 1

| | | | | KD (nM) | |
|---|---|---|---|---|---|
| Sequence of peptide | SEQ ID NO: | ka | kd | 1:1 binding | Equilibrium value |
| DCAYHXaa1GELVWCT-$NH_2$ | 1, wherein Xaa1 is R | 4.57E+05 | 0.0248 | 54 | 64.5 |
| GPRCAYHXaa1GELVWCSFH-$NH_2$ | 4, wherein Xaa1 is R | 8.40E+05 | 0.0353 | 42 | 56 |
| GPDCAYHXaa1GELVWCTFH-$NH_2$ | 2, wherein Xaa1 is R | 1.57E+06 | 0.0144 | 9.1 | 10 |
| GPDCAYHXaa1GELVWCTFH-$NH_2$ | 2, wherein Xaa1 is L | 1.7E+05 | 0.014 | 8.1 | — |
| GPDCAYHXaa1GELVWCTFH-$NH_2$ | 2, wherein Xaa1 is K | 1.25E+06 | 0.195 | 156 | 131 |
| GPDCAYHXaa1GELVWCTFH-$NH_2$ | 2, wherein Xaa1 is K (Acetyl) | 4.4E+05 | 0.12 | 2700 | 2800 |

Affinities of various peptides (All peptides used were those blocked at the N-terminus with biotinylated PEG4). "K(Acetyl)" in the last line means an acetylated lysine residue.

Example 2: Preparation of IgG-Binding Peptide Cross-Linked Via Linker

An NH2-PEG4-modified synthetic peptide GPDCAYH (Xaa1)GELVWCTFH (SEQ ID NO:2, wherein Xaa1 was arginine and the C-terminus was amidated) was synthesized on peptide synthesis beads (Rink-amide-Chemmatrix resin, Biotage) by Fmoc solid-phase synthesis in accordance with an ordinary method.

The peptide is excised from the resin and deprotected to obtain the resulting peptide. Then, 65 mg of the resulting peptide (15.6 μmol) was dissolved in 5 mL of a phosphate buffer (pH=7.3) containing 6 M guanidium chloride (Gn.HCl), and 1,3-dichloro-2-propanone (2.9 mg, 23.4 μmol, 1.5 molar equivalent) dissolved in 120 μL of acetonitrile was added therein. The mixture was stirred at room temperature for 1 hour, and then, the completion of the reaction was checked by HPLC analysis. The reaction solution was purified directly by HPLC to obtain a cyclized peptide (33 mg, 7.8 μmol, yield 50%).

The procedures above provided an N-terminally PEG4-modified and C-terminally amidated peptide (Peptide a) including an amino acid sequence represented by GPDCAYH(Xaa1)GELVWCTFH (SEQ ID NO:2, wherein Xaa1 was arginine and the C-terminus was amidated), in which sulfide groups in the two outermost cysteine residues were connected via a linker represented by the following formula:

[Chemical Formula 11]

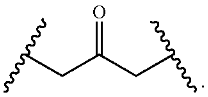

In addition, 1.1 mg of a peptide prepared in a similar manner as above (Fmoc-HN-PEG4-GPDCAYH(Xaa1)GELVWCTFH (SEQ ID NO:2, wherein Xaa1 was arginine and the C-terminus was amidated)) was dissolved in 220 μL of DMF (2 mM), and 22 μL of 10 mM thiocarbonyldiimidazole (0.5 molar equivalent) dissolved in acetonitrile was added, followed by stirring on ice for 2.5 hours. The completion of the reaction was checked by HPLC analysis and the reaction solution was purified directly by HPLC to obtain a cyclized peptide (Peptide b) (0.3 mg, yield 27%), in which sulfide groups in the two cysteine residues were connected via a linker represented by the following formula:

[Chemical Formula 12]

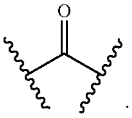

This peptide was measured for affinity for IgG as in Example 1, and Kd was revealed to be 1 μM.

Example 3: Separation of Human Serum-Derived γ-Globulin

A dichloroacetone-cross-linked peptide was immobilized to an NHS-activated prepacked column (GE Healthcare) to carry out various evaluations to assess whether the dichloroacetone-cross-linked peptide can be used as an affinity ligand for human antibody purification.

The peptide-immobilized column was prepared by the following procedures. A syringe was used to feed a solution.

To a 1-mL capacity NHS-activated prepacked column, 5 mL of 1 mM hydrochloric acid was fed to remove an isopropanol solution in the column. Then, 1 mL of a 1.0 mg/mL peptide solution (a 100 mg/mL solution of Peptide a prepared in Example 2 dissolved in DMSO was diluted 100 times with a coupling solution (20 mM carbonate buffer, 50 mM sodium chloride, pH 8.3)) was fed to the column to immobilize the peptide thereto at room temperature for 1 hour. Unreacted NHSs were then blocked with 5 mL of 1 M Tris (pH 8.0) at room temperature for 1 hour. Finally, 5 mL of an adsorption solution (20 mM phosphate buffer, 150 mM sodium chloride, pH 7.4) was fed to the column to use the column for the following chromatographic assessment.

The prepared peptide-immobilized column was connected to a liquid chromatography system AKTAexplore (GE Healthcare) and equilibrated with the adsorption solution. Then, a 1 mg/mL solution of human serum-derived γ-globulin (Wako) dissolved in the adsorption solution was fed to the column at a flow rate of 1 mL/min for 1 min. Furthermore, the column was washed with the adsorption solution, and the adsorbed components were eluted by feeding an acidic elution solution (20 mM citric acid, pH 2.5). The elution of proteins from the column was detected by absorbance at 280 nm. Experimental results are illustrated in FIG. 1.

As illustrated in FIG. 1, along with the decrease of pH, elution of the human serum-derived γ-globulin adsorbed in the column was confirmed, revealing that the peptide prepared in Example 2 can be used as a ligand for an affinity column.

Example 4: Competitive Elution with Peptide

To the column prepared by the same method as in Example 3, 1 mg of human-derived serum γ-globulin was fed to adsorb the globulin thereto. The column was washed with the adsorption solution, and then 2.5 mL of a 0.4 mg/mL solution of Peptide a prepared in Example 2 dissolved in the adsorption solution was fed to the column. Each fraction fractionated in 0.5 mL was subjected to SDS-PAGE under reductive conditions in accordance with an ordinary method. Proteins were detected by CBB staining. For comparison, similar operations were carried out also for citric acid elution.

Figure 2:
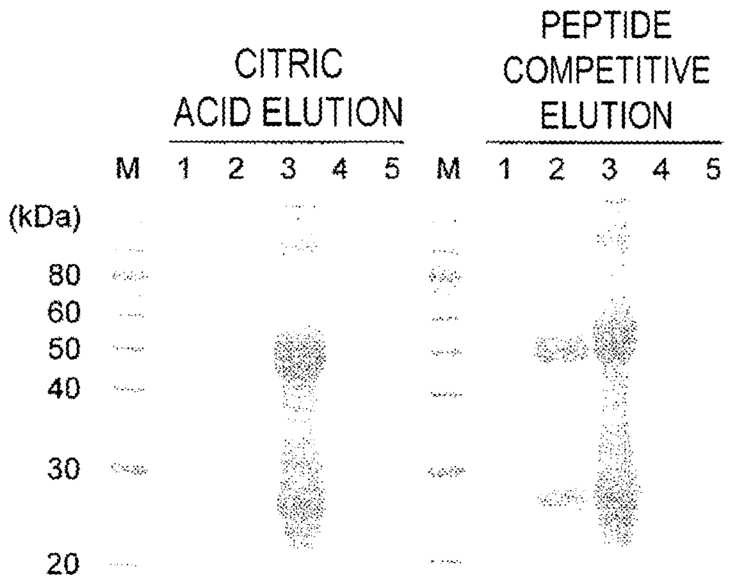
FIG. 2 illustrates results of SDS-PAGE of fractions fractionated in 0.5 mL that are obtained by eluting proteins with citric acid or the IgG-binding peptide from the column with immobilized peptide prepared in Example 3. The proteins were detected by CBB staining.

As illustrated in FIG. 2, bands around 25 kDa and around 50 kDa indicating the light chain (L-chain) and the heavy chain (H-chain), respectively, were confirmed, revealing that the peptide solution can be used as a means for elution.

Example 5: Dynamic Binding Capacity (DBC) Measurement

Three types of columns with different amounts of immobilized peptide (1 mg, 4 mg, and 10 mg) were prepared by a similar method as in Example 3. Peptide solutions, 4 mg/mL and 10 mg/mL, were prepared to use for the immobilization.

Figure 3:
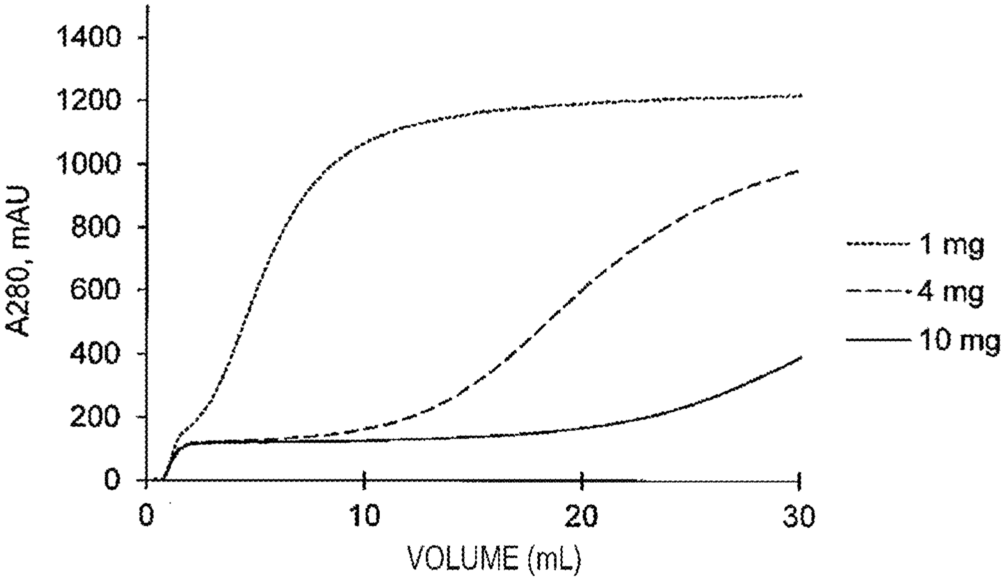
FIG. 3 illustrates DBC measurement results when three columns with different amounts of immobilized peptide (1 mg, 4 mg, and 10 mg) were equilibrated with an adsorption solution, and then 1 mg/mL human serum-derived γ-globulin dissolved in the adsorption solution was fed through the columns at a flow rate of 1 mL/min (residence time of 1 min). DBC was determined from an amount of the sample fed until the absorbance value at 280 nm, from which that of non-adsorbed components was deducted, reached 10% of the absorbance of the entire sample.

After each column was equilibrated with the adsorption solution, a 1 mg/mL solution of human serum-derived γ-globulin (Wako) dissolved in the adsorption solution was fed to each column at a flow rate of 1 mL/min, 0.4 mL/min, or 0.2 mL/min (residence time of 1 min, 2.5 min, or 5 min). DBC was determined from an amount of the sample fed until the absorbance value at 280 nm, from which that of non-adsorbed components was deducted, reached 10% of the absorbance of the entire sample. Chromatograms at a flow rate of 1 mL/min are illustrated in FIG. 3, and DBCs are summarized in Table 2. In addition, the same measurement was also carried out for a commercially available Protein A support MabSelect (GE Healthcare) for comparison.

TABLE 2

| | Residence time | | |
|---|---|---|---|
| Immobilized amount | 1 min | 2.5 min | 5 min |
| 1 mg | 2.3 | 3.4 | 7.0 |
| 4 mg | 12.1 | 15.8 | 23.1 |
| 10 mg | 23.1 | 29.5 | 31.4 |
| MabSelect | 10.0 | 24.3 | 43.7 |

As illustrated in FIG. 3 and as shown in Table 2, it was revealed that DBC is increased by increasing the immobilized peptide amount. Although DBC of the 10-mg peptide-immobilized column was lower than that of MabSelect at a low flow rate where the residence time was 5 min, it was significantly higher at a high flow rate where the residence time was 1 min, suggesting the column would be suitable for purification at high flow rate (Table 2).

Example 6: Evaluation of Alkali Resistance

To a 1-mg peptide-immobilized 1-mL column prepared by the same method as in Example 3, 5 mL of 0.1 M sodium hydroxide solution was fed. The column was then washed with the adsorption solution and DBC was measured at a flow rate of 1 mL/min as in Example 5. Subsequently, a cycle of the treatment with the sodium hydroxide solution and the DBC measurement was repeated five times to evaluate the alkali resistance. The variation rate of DBC was determined based on the DBC before the sodium hydroxide treatment as 100%.

Comparative Example 1

As Comparative Example 1, a column with 1 mg of a peptide cross-linked by a disulfide bond immobilized thereon was prepared, and the alkali resistance evaluation was carried out as in Example 5.

Figure 4:
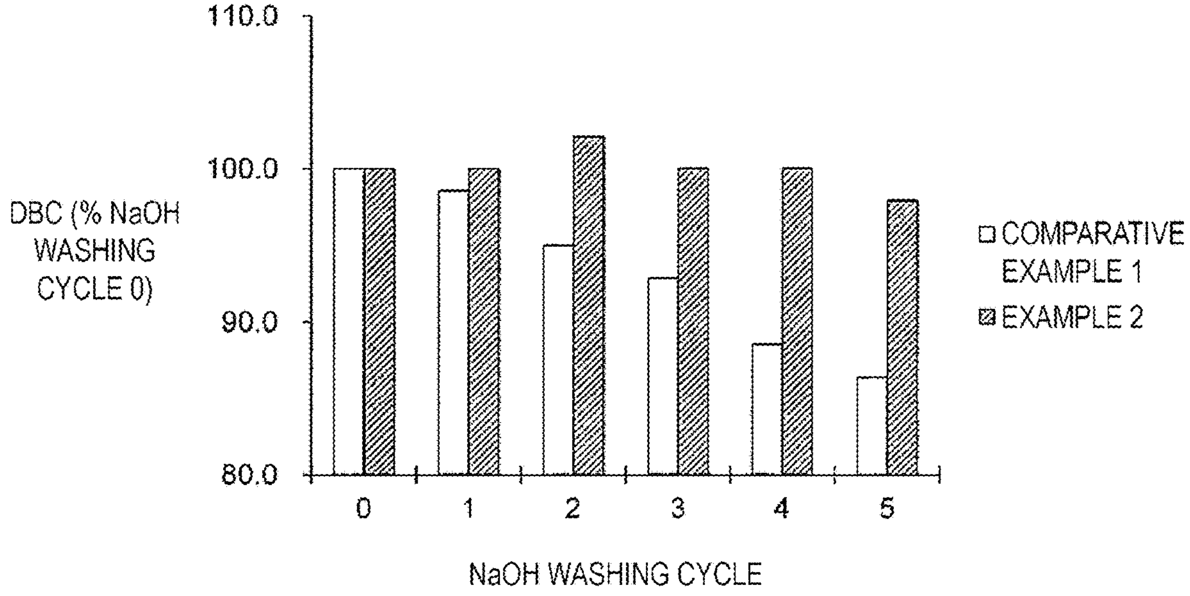
FIG. 4 illustrates measurement results of DBC of an IgG-binding peptide cross-linked via a linker, prepared in Example 2, and an IgG-binding peptide cross-linked by disulfide, prepared in Comparative Example 1, both of which were treated with sodium hydroxide.

Results from Example 5 and Comparative Example 1 are illustrated in FIG. 4, and measured values are summarized in Table 3.

TABLE 3

| | DBC 10% (% NaOH washing cycle 0) | | DBC 10% (mg/mL) | |
|---|---|---|---|---|
| (% NaOH washing cycle) | Comparative Example 1 | Example 5 | Comparative Example 1 | Example 5 |
| 0 | 100.0 | 100.0 | 14.0 | 4.8 |
| 1 | 98.6 | 100.0 | 13.8 | 4.8 |
| 2 | 95.0 | 102.1 | 13.3 | 4.9 |
| 3 | 92.9 | 100.0 | 13.0 | 4.8 |
| 4 | 88.6 | 100.0 | 12.4 | 4.8 |
| 5 | 86.4 | 97.9 | 12.1 | 4.7 |

As illustrated in FIG. 4 and as shown in Table 3, the peptide cross-linked by a disulfide bond showed a decrease in DBC to 86.4% by the five sodium hydroxide treatments (Comparative Example 1). In contrast, the dichloroacetone-cross-linked peptide showed no decrease in DBC, revealing that the peptide has high alkali resistance.

INDUSTRIAL APPLICABILITY

The peptide included in the solid-phase support of the present invention has improved stability by cross-linking sulfide groups in cysteine residues by a linker having a specific structure. Accordingly, the IgG binding capacity of the solid-phase support of the present invention is not likely to be diminished due to a process, such as an alkaline washing step, and thus the solid-phase support of the present invention can be used for an efficient purification of IgG and production of IgG that is used also as a pharmaceutical.

All publications, patents, and patent applications cited in the present specification are incorporated by reference in the present specification as they are.

The invention claimed is:

1. A solid-phase support with a peptide immobilized thereon, the peptide being capable of binding to human IgG, wherein the peptide comprises an amino acid sequence comprising from 13 to 17 amino acid residues, the amino acid sequence of Formula I:

$$(X_{1-3})\text{-C-}(X_2)\text{-H-(Xaa1)-G-(Xaa2)-L-V-W-C-}(X_{1-3}) \quad \text{(I)}$$

wherein each X is independently any amino acid residue other than cysteine,

C is a cysteine residue,

H is a histidine residue,

Xaa1 is an arginine residue, a lysine residue, a leucine residue, or an asparagine residue, or a derivative thereof, G is a glycine residue, Xaa2 is a glutamic acid residue or an asparagine residue, L is a leucine residue, V is a valine residue, and W is a tryptophan residue; and sulfide groups in the two outermost cysteine residues in the peptide are connected via a linker selected from the group consisting of formulas:

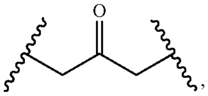,
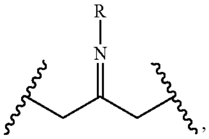,
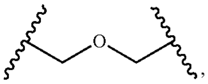,
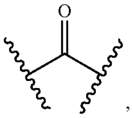, and
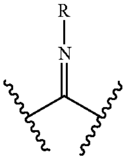

where R is a substituted or unsubstituted C1 to C6 alkyl.

2. The solid-phase support according to claim 1, wherein the peptide comprises an amino acid sequence comprising from 13 to 17 amino acid residues, the amino acid sequence of Formula II:

$$(X_{1-3})\text{-C-(Xaa3)-(Xaa4)-H-(Xaa1)-G-(Xaa2)-L-V-W-C-}(X_{1-3}) \quad \text{(II)}$$

wherein each X is independently any amino acid residue other than cysteine,

C is a cysteine residue,

H is a histidine residue,

Xaa1 is an arginine residue, a lysine residue, a leucine residue, an asparagine residue, or a derivative thereof, G is a glycine residue, Xaa2 is a glutamic acid residue or an asparagine residue, L is a leucine residue, V is a valine residue, W is a tryptophan residue, Xaa3 is an alanine residue, a serine residue, or a threonine residue, and Xaa4 is a tyrosine residue or a tryptophan residue.

3. The solid-phase support according to claim 1, wherein the peptide comprises an amino acid sequence comprising from 13 to 17 amino acid residues, the amino acid sequence of Formula III:

$$(X_{1-3})\text{-C-A-Y-H-(Xaa1)-G-E-L-V-W-C-}(X_{1-3}) \quad \text{(III)}$$

wherein each X is independently any amino acid residue other than cysteine,

C is a cysteine residue,

A is an alanine residue,

Y is a tyrosine residue,

H is a histidine residue,

Xaa1 is an arginine residue, a lysine residue, a leucine residue, or an asparagine residue, or a derivative thereof, G is a glycine residue, E is a glutamic acid residue, L is a leucine residue, V is a valine residue, and W is a tryptophan residue.

4. The solid-phase support according to claim 1, wherein each amino acid residue at positions 1 to 3 and 15 to 17 of Formula I is as follows:

the amino acid residue of X at position 1 is S, G, F, or absent, the amino acid residue of X at position 2 is D, G, A, S, P, homocysteine, or absent, the amino acid residue of X at position 3 is S, D, T, N, E, or R, the amino acid residue of X at position 15 is S, T, or D, the amino acid residue of X at position 16 is H, G, Y, T, N, D, F, homocysteine, or absent, and the amino acid residue of X at position 17 is Y, F, H, M, or absent.

5. The solid-phase support according to claim 4, wherein the peptide is selected from the group consisting of the amino acid sequences of 1) to 14):

```
                          (SEQ ID NO: 1)
 1) DCAYH(Xaa1)GELVWCT,

                          (SEQ ID NO: 2)
 2) GPDCAYH(Xaa1)GELVWCTFH,

                          (SEQ ID NO: 3)
 3) RCAYH(Xaa1)GELVWCS,

                          (SEQ ID NO: 4)
 4) GPRCAYH(Xaa1)GELVWCSFH,

                          (SEQ ID NO: 5)
 5) SPDCAYH(Xaa1)GELVWCTFH,

                          (SEQ ID NO: 6)
 6) GDDCAYH(Xaa1)GELVWCTFH,

                          (SEQ ID NO: 7)
 7) GPSCAYH(Xaa1)GELVWCTFH,

                          (SEQ ID NO: 8)
 8) GPDCAYH(Xaa1)GELVWCSFH,

                          (SEQ ID NO: 9)
 9) GPDCAYH(Xaa1)GELVWCTHH,

                         (SEQ ID NO: 10)
10) GPDCAYH(Xaa1)GELVWCTFY,

                         (SEQ ID NO: 11)
11) SPDCAYH(Xaa1)GELVWCTFY,

                         (SEQ ID NO: 12)
12) SDDCAYH(Xaa1)GELVWCTFY,

                         (SEQ ID NO: 13)
13) RGNCAYH(Xaa1)GQLVWCTYH,

                         (SEQ ID NO: 14)
14) G(Xaa2)DCAYH(Xaa1)GELVWCT(Xaa2)H,
```

with the proviso that Xaa1 is an arginine residue, a lysine residue, a leucine residue, an asparagine residue, or a derivative thereof, and Xaa2 is homocysteine.

6. The solid-phase support according to claim 1, wherein the peptide comprises an amino acid sequence comprising 13 amino acid residues, the amino acid sequence being of Formula IV:

D-C-(Xaa3)-(Xaa4)-H-(Xaa1)-G-(Xaa2)-L-V-W-C-T (IV)

wherein

D is an aspartic acid residue,

C is a cysteine residue,

H is a histidine residue,

Xaa1 is an arginine residue, a lysine residue, a leucine residue, an asparagine residue, or a derivative thereof, G is a glycine residue, Xaa2 is a glutamic acid residue or an asparagine residue, L is a leucine residue, V is a valine residue, W is a tryptophan residue, T is a threonine residue, Xaa3 is an alanine residue or a threonine residue, and Xaa4 is a tyrosine residue or a tryptophan residue.

7. The solid-phase support according to claim 6, wherein the peptide is selected from the group consisting of amino acid sequences of 1) to 4):

```
                                      (SEQ ID NO: 15)
1)           DCTYH(Xaa1)GNLVWCT,

                                      (SEQ ID NO: 16)
2)           DCAYH(Xaa1)GNLVWCT,

                                      (SEQ ID NO: 17)
3)           DCTYH(Xaa1)GELVWCT,

                                      (SEQ ID NO: 18)
4)           DCAWH(Xaa1)GELVWCT,
```

with the proviso that Xaa1 is an arginine residue, a lysine residue, a leucine residue, or an asparagine residue, or a derivative thereof.

8. The solid-phase support according to claim 1, wherein Xaa1 is an arginine residue, a lysine residue, an acylated derivative of lysine, or a leucine residue.

9. The solid-phase support according to claim 1, wherein the peptide comprises the amino acid sequence: GPDCAYHRGELVWCTFH (SEQ ID NO:31).

10. The solid-phase support according to claim 1, wherein the linker is

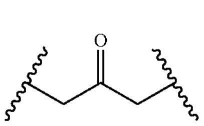

or

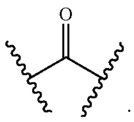

.

11. The solid-phase support according to claim 1, wherein the N-terminus of the peptide is PEGylated.

12. The solid-phase support according to claim 1, wherein the C-terminus of the peptide is amidated.

13. The solid-phase support according to claim 1, wherein the peptide is multimerized.

14. The solid-phase support according to claim 13, wherein the multimer of the peptide comprises a spacer between the peptides.

15. The solid-phase support according to claim 1, comprising a spacer between the peptide and the solid phase.

16. An IgG separation column, comprising the solid-phase support of in claim 1.

17. A kit for purifying IgG, comprising the solid-phase support of claim 1.

18. A solid-phase support with a peptide immobilized thereon, the peptide being capable of binding to human IgG;

wherein the peptide comprises an amino acid sequence comprising 13 amino acid residues, the amino acid sequence of Formula V:

D-C-(Xaa2)-(Xaa3)-(Xaa4)-(Xaa1)-G-(Xaa5)-L-(Xaa6)-W-C-T (V)

wherein

D is an aspartic acid residue,

C is a cysteine residue,

G is a glycine residue,

L is a leucine residue,

W is a tryptophan residue,

T is a threonine residue,

Xaa1 is an arginine residue, a lysine residue, a leucine residue, or an asparagine residue, or a derivative thereof, Xaa2 is an alanine residue, a serine residue, or a threonine residue, Xaa3 is a tryptophan residue or a tyrosine residue, Xaa4 is a histidine residue, an arginine residue, a serine residue, or a threonine residue, Xaa5 is a glutamic acid residue, an asparagine residue, an arginine residue, or an aspartic acid residue, and Xaa6 is an isoleucine residue or a valine residue; and sulfide groups in the two outermost cysteine residues in the peptide are connected via a linker selected from the group consisting of formulas:

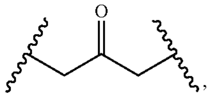

,

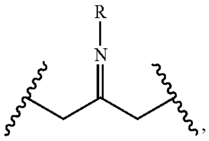

,

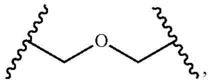

,

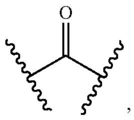

, and

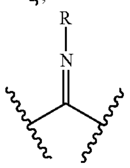

where R is a substituted or unsubstituted C1 to C6 alkyl.

19. A method for purifying IgG, comprising:

binding IgG to the solid-phase support of claim 1; and eluting the bound IgG to collect the IgG.

* * * * *